United States Patent
Rampf et al.

(10) Patent No.: US 10,457,589 B2
(45) Date of Patent: Oct. 29, 2019

(54) LITHIUM SILICATE DIOPSIDE GLASS CERAMICS

(71) Applicant: Ivoclar Vivadent AG, Schaan (LI)

(72) Inventors: Markus Rampf, Lachen (CH);
Christian Ritzberger, Grabs (CH);
Marc Dittmer, Feldkirch (AT);
Wolfram Höland, Schaan (LI); Marcel Schweiger, Chur (CH)

(73) Assignee: Ivoclar Vivadent AG, Schaan (LI)

( * ) Notice: Subject to any disclaimer, the term of this patent is extended or adjusted under 35 U.S.C. 154(b) by 16 days.

(21) Appl. No.: 15/546,455

(22) PCT Filed: Jan. 21, 2016

(86) PCT No.: PCT/EP2016/051204
§ 371 (c)(1),
(2) Date: Jul. 26, 2017

(87) PCT Pub. No.: WO2016/120146
PCT Pub. Date: Aug. 4, 2016

(65) Prior Publication Data
US 2018/0009701 A1    Jan. 11, 2018

(30) Foreign Application Priority Data
Jan. 30, 2015 (EP) .................................... 15153296

(51) Int. Cl.
*C03C 10/00* (2006.01)
*A61K 6/027* (2006.01)
(Continued)

(52) U.S. Cl.
CPC ........ *C03C 10/0027* (2013.01); *A61K 6/0273* (2013.01); *C03C 3/078* (2013.01);
(Continued)

(58) Field of Classification Search
CPC ......... C03C 3/095; C03C 3/076; C03C 3/097; C03C 10/0009; C03C 10/0027;
(Continued)

(56) References Cited

U.S. PATENT DOCUMENTS

| | | | |
|---|---|---|---|
| 2,684,911 A | 7/1954 | Stookey |
| 3,006,775 A | 10/1961 | Chen |

(Continued)

FOREIGN PATENT DOCUMENTS

| | | |
|---|---|---|
| CA | 2163792 A1 | 12/1994 |
| CA | 2213390 A1 | 3/1998 |

(Continued)

OTHER PUBLICATIONS

Salman et al. Crystallization characteristics and physico-chemical properties of the glasses based on $Li_2O$—CaO—$SiO_2$ eutectic (954° C.) system containing magnesium oxide. Ceramics International, vol. 34, Issue 8, Dec. 2008, pp. 1819-1828.*

(Continued)

*Primary Examiner* — Noah S Wiese
(74) *Attorney, Agent, or Firm* — Ann M. Knab; Thad McMurray

(57) ABSTRACT

Lithium silicate-diopside glass ceramics are described which are characterized by a controllable translucence and can be satisfactorily processed mechanically and therefore can be used in particular as restoration material in dentistry.

23 Claims, 1 Drawing Sheet

(51) Int. Cl.
    *C03C 3/078*     (2006.01)
    *C03C 3/097*     (2006.01)
    *C03C 3/112*     (2006.01)
    *C03C 4/00*     (2006.01)
    *C03C 8/02*     (2006.01)
    *C03C 8/06*     (2006.01)
    *C03C 8/08*     (2006.01)
    *C03B 19/06*     (2006.01)

(52) U.S. Cl.
CPC ............. *C03C 3/097* (2013.01); *C03C 3/112* (2013.01); *C03C 4/0021* (2013.01); *C03C 8/02* (2013.01); *C03C 8/06* (2013.01); *C03C 8/08* (2013.01); *C03C 10/0009* (2013.01); *C03C 10/0054* (2013.01); *C03B 19/06* (2013.01); *C03C 2205/06* (2013.01)

(58) Field of Classification Search
CPC ......... C03C 4/0021; A61K 6/02; A61C 13/00; A61C 13/083; A61C 13/0022; C03B 32/02
See application file for complete search history.

(56) References Cited

U.S. PATENT DOCUMENTS

| | | | |
|---|---|---|---|
| 3,022,180 A | 2/1962 | Morrissey et al. | |
| 3,161,528 A | 12/1964 | Eppler | |
| 3,252,778 A | 5/1966 | Goodman et al. | |
| 3,804,608 A | 4/1974 | Gaskell et al. | |
| 3,816,704 A | 6/1974 | Borom et al. | |
| 3,977,857 A | 8/1976 | Mattox | |
| 4,155,888 A | 5/1979 | Mooth | |
| 4,189,325 A | 2/1980 | Barrett et al. | |
| 4,414,282 A | 11/1983 | McCollister et al. | |
| 4,473,653 A | 9/1984 | Rudoi | |
| 4,480,044 A | 10/1984 | McAlinn | |
| 4,515,634 A | 5/1985 | Wu et al. | |
| 4,560,666 A | 12/1985 | Yoshida et al. | |
| 4,643,982 A | 2/1987 | Kasuga et al. | |
| 4,671,770 A | 6/1987 | Bell et al. | |
| 4,871,384 A | 10/1989 | Kasuga et al. | |
| 4,963,707 A | 10/1990 | Zyokou et al. | |
| 4,977,114 A | 12/1990 | Horinouchi et al. | |
| 5,066,619 A | 11/1991 | Kasuga et al. | |
| 5,176,961 A | 1/1993 | Crooker et al. | |
| 5,219,799 A | 6/1993 | Beall et al. | |
| 5,232,878 A | 8/1993 | Kasuga et al. | |
| 5,246,889 A | 9/1993 | Kasuga et al. | |
| 5,356,436 A | 10/1994 | Nonami et al. | |
| 5,507,981 A | 4/1996 | Petticrew | |
| 5,628,564 A | 5/1997 | Nenyei et al. | |
| 5,691,256 A | 11/1997 | Taguchi et al. | |
| 5,698,482 A | 12/1997 | Frank et al. | |
| 5,702,514 A | 12/1997 | Petticrew | |
| 5,707,777 A | 1/1998 | Aoai et al. | |
| 5,711,763 A | 1/1998 | Nonami et al. | |
| 5,872,069 A | 2/1999 | Abe | |
| 5,874,376 A | 2/1999 | Taguchi et al. | |
| 5,938,959 A | 8/1999 | Wang | |
| 5,968,856 A | 10/1999 | Schweiger et al. | |
| 6,027,791 A * | 2/2000 | Higashi ................ | H05K 3/3436 257/693 |
| 6,048,589 A | 4/2000 | Suzuki | |
| 6,066,584 A | 5/2000 | Krell et al. | |
| 6,095,682 A | 8/2000 | Hollander et al. | |
| 6,106,747 A | 8/2000 | Wohlwend | |
| 6,121,175 A | 9/2000 | Drescher et al. | |
| 6,157,004 A | 12/2000 | Bizzio | |
| 6,163,020 A | 12/2000 | Bartusch et al. | |
| 6,174,827 B1 | 1/2001 | Goto et al. | |
| 6,252,202 B1 | 6/2001 | Zychek | |
| 6,267,595 B1 | 7/2001 | Gratz | |
| 6,270,876 B1 | 8/2001 | Abe et al. | |
| 6,287,121 B1 | 9/2001 | Guiot et al. | |
| 6,342,458 B1 | 1/2002 | Schweiger et al. | |
| 6,376,397 B1 | 4/2002 | Petticrew | |
| 6,420,288 B2 | 7/2002 | Clausbruch et al. | |
| 6,441,346 B1 | 8/2002 | Zychek | |
| 6,455,451 B1 | 9/2002 | Brodkin et al. | |
| 6,485,849 B2 | 11/2002 | Petticrew | |
| 6,514,893 B1 | 2/2003 | Schweiger et al. | |
| 6,517,623 B1 | 2/2003 | Brodkin et al. | |
| 6,593,257 B1 | 7/2003 | Nagata et al. | |
| 6,802,894 B2 | 10/2004 | Brodkin et al. | |
| 6,818,573 B2 | 11/2004 | Petticrew | |
| 7,162,321 B2 | 1/2007 | Luthardt et al. | |
| 7,316,740 B2 * | 1/2008 | Schweiger ......... | C03C 10/0027 106/35 |
| 7,452,836 B2 | 11/2008 | Apel et al. | |
| 7,655,586 B1 | 2/2010 | Brodkin et al. | |
| 7,806,694 B2 | 10/2010 | Brodkin et al. | |
| 7,816,291 B2 | 10/2010 | Schweiger et al. | |
| 7,867,930 B2 | 1/2011 | Apel et al. | |
| 7,867,933 B2 | 1/2011 | Apel et al. | |
| 7,871,948 B2 | 1/2011 | Apel et al. | |
| 7,892,995 B2 | 2/2011 | Castillo | |
| 7,993,137 B2 | 8/2011 | Apel et al. | |
| 8,042,358 B2 | 10/2011 | Schweiger et al. | |
| 8,047,021 B2 | 11/2011 | Schweiger et al. | |
| 8,444,756 B2 | 5/2013 | Schweiger et al. | |
| 2001/0006174 A1 | 7/2001 | Brennan | |
| 2001/0031446 A1 | 10/2001 | Petticrew | |
| 2002/0010063 A1 | 1/2002 | Schweiger et al. | |
| 2002/0022563 A1 | 2/2002 | Schweiger et al. | |
| 2002/0031670 A1 | 3/2002 | Goto et al. | |
| 2002/0035025 A1 | 3/2002 | Schweiger et al. | |
| 2002/0160694 A1 | 10/2002 | Wood et al. | |
| 2003/0073563 A1 | 4/2003 | Brodkin et al. | |
| 2003/0215770 A1 | 11/2003 | Sekino et al. | |
| 2004/0182538 A1 | 9/2004 | Lambrecht | |
| 2005/0079226 A1 | 4/2005 | Gonda et al. | |
| 2005/0098064 A1 | 5/2005 | Schweiger et al. | |
| 2005/0127544 A1 | 6/2005 | Brodkin et al. | |
| 2006/0082033 A1 | 4/2006 | Hauptmann et al. | |
| 2006/0139091 A1 | 6/2006 | Fratti | |
| 2006/0257823 A1 | 11/2006 | Pfeiffer et al. | |
| 2006/0257824 A1 | 11/2006 | Pfeiffer et al. | |
| 2007/0023971 A1 | 2/2007 | Saha et al. | |
| 2008/0120994 A1 | 5/2008 | Schweiger et al. | |
| 2008/0199823 A1 | 8/2008 | Miller | |
| 2009/0023574 A1 | 1/2009 | Holand et al. | |
| 2009/0038344 A1 | 2/2009 | Apel et al. | |
| 2009/0038508 A1 | 2/2009 | Apel et al. | |
| 2009/0042166 A1 | 2/2009 | Craig et al. | |
| 2009/0256274 A1 | 10/2009 | Castillo | |
| 2009/0258778 A1 | 10/2009 | Castillo | |
| 2010/0083706 A1 | 4/2010 | Castillo | |
| 2011/0076693 A1 | 3/2011 | Lee et al. | |
| 2011/0256409 A1 | 10/2011 | Ritzberger et al. | |
| 2012/0094822 A1 | 4/2012 | Castillo et al. | |
| 2012/0148988 A1 | 6/2012 | Castillo et al. | |
| 2012/0248642 A1 | 10/2012 | Ritzberger et al. | |
| 2012/0309607 A1 | 12/2012 | Durschang et al. | |
| 2014/0141960 A1 | 5/2014 | Borczuch-Laczka et al. | |
| 2014/0228196 A1 * | 8/2014 | Ritzberger ............ | C03C 3/095 501/32 |

FOREIGN PATENT DOCUMENTS

| | | |
|---|---|---|
| CA | 2252660 A1 | 5/1999 |
| DE | 2451121 A1 | 5/1975 |
| DE | 4303458 C1 | 1/1994 |
| EP | 1152641 A2 | 11/2001 |
| GB | 752243 A | 7/1956 |
| GB | 2284655 A | 6/1995 |
| JP | H10323354 A | 12/1998 |
| JP | 11-74418 A | 3/1999 |
| JP | 2005-062832 A | 3/2005 |

(56) References Cited

FOREIGN PATENT DOCUMENTS

| WO | 2007028787 A1 | 3/2007 |
|---|---|---|
| WO | 2012172316 A3 | 12/2012 |

OTHER PUBLICATIONS

International Preliminary Report on Patentability of PCT/EP2016/051204, dated Aug. 1, 2017, 18 pages.

Apel, E., et al., "Influence of ZrO2 on the crystallization and properties of lithium disilicate glass-ceramics derived from multi-component system", Journal of European Ceramic Society, 2007, 27, 1571-1577.

Durschang, Dr. Bernhard, "Report of Results", Fraunhofer Institute for Silicate Research ISC Glass and Mineral Materials, 2015.

Mcmillan, P.W. et al., "The Structure and Properties of a Lithium Zinc Silicate Glass-Ceramic", Journal of Material Science 1966, I. 269-279.

Deubener, J. et al., "Induction time analysis of nucleation and crystal grown in di- and metasilicate glasses", Journal of Non-Crystalline Solids 1993, 163, 1-12.

Holand, W. et al., "Glass-ceramic technology", American Chemical Society 2002, Westerville OH, USA.

Holand, W. et al., "Control of nucleation in glass ceramics", Phil. Trans. Soc. Lond. A 2003, 361, 575-589.

Holand, W. et al., "Principles and phenomena of bioengineering with glass-ceramics of dental restoration", Journal of the European Ceramics Society 2007, 27, 1571-1577.

Ivoclar Vivadent Inc., IPS e.max lithium disilicate, 627329, Rev. Feb. 2009.

Borom, M.P., et al., "Strength and Microstructure in Lithium Disilicate Glass Ceramics", J. Am. Ceram. Soc., 1975,58, 385-391.

Von Clausbruch, et al., "Effect of ZnO on the Crystallization, Microstructure, and Properties of Glass-Ceramics in the SiO2—Li2O—K2O—P2O5 System," Glastech. Ber. Glass Sci. Technol. 74(8):223-229(2001).

Von Clausbruch, et al., "Effect of P2O5 on the Crystallization and Microstructure of Glass-Ceramics in the SiO2—Li2O—Zn)—P2O5 System," Glastech. Ber. Glass Sci. Technol. 74(8):223-229(2001).

Stookey, S.D., "Chemical Machining of Photosensitive Glass," Ind. Eng. Chem. 45:115-118 (1993).

Oliveria et al., "Sintering and Crystallization of a GlassPowder in the Li2O—ZrO2—SiO2 System," J. Amer. Ceramic Soc. 81(3):777-780 (1998).

Montedo, et al., "Low Thermal Expansion Sintered LZSA Glass-Ceramics," American Ceramic Society Bulletin, vol. 87, No. 7, pp. 34-40. 2008.

Giassi, et al., "Injection Moulding of LiO2—ZrO2—SiO2—Al2O3 (LZSA) Glass Ceramics," Glass Technol., 46(3), 277-280 (2005).

http://en.wikipedia.org/wiki/Nucleation ; Sep. 20, 2012.

Salman et al., "Crystallization characteristics and physico-chemical properties of the glasses based on Li2O—CaO—SiO2 eutectic (954° C.) system containing magnesium oxide," Ceramics International, 34 (2008) 1819-1828.

Salman et al., "The influence of Al2O3, MgO and ZnO on the crystallization characteristics and properties of lithium calcium silicate glasses and glass-ceramics," Materials Chemistry and Physics, 112 (2008) 949-953.

Salman et al., "Crystallization behaviour and properties of multicomponent strontium—Containing lithia calcia silicate glasses," Ceramics International, 36 (2010) 2307-2314.

Dittmer, Dr. Marc, "Glasses and glass-ceramics in the system of MgO—Al2O3—SiO2 with ZrO2 as nucleating agent," Dissertation, 2011.

* cited by examiner

US 10,457,589 B2

LITHIUM SILICATE DIOPSIDE GLASS CERAMICS

CROSS-REFERENCE TO RELATED APPLICATIONS

This application is a National Stage application of International patent application PCT/EP2016/051204 filed on Jan. 21, 2016, which claims priority to European patent application No. 15153296.7 filed on Jan. 30, 2015, the disclosures of which are incorporated herein by reference in their entirety.

FIELD OF THE INVENTION

The invention relates to lithium silicate-diopside glass ceramic which is suitable in particular for use in dentistry, preferably for the preparation of dental restorations, as well as to precursors for the preparation of the glass ceramic.

BACKGROUND OF THE INVENTION

Glass ceramics with a lithium silicate crystal phase and the use thereof in dental products are known from the state of the art. For example, EP 1 505 041 describes lithium silicate glass ceramics which, in the form of lithium metasilicate glass ceramics, are processed by means of CAD/CAM processes to form the desired dental restorations, wherein a subsequent heat treatment leads to the conversion of the lithium metasilicate ($Li_2SiO_3$) phase into lithium disilicate ($Li_2Si_2O_5$) phase and thus to the formation of high-strength lithium disilicate glass ceramic. Machining of the glass ceramic after the formation of the lithium disilicate phase is, in particular because of the high strength thereof, time-consuming and associated with high tool wear.

Glass ceramics which contain diopside, $CaMgSi_2O_6$, as crystal phase are known. Diopside can form as intermediate phase in amphibole glass ceramics (Höland, Beall, "Glass-Ceramic Technology", Wiley, USA, 2nd Edition, 2012, p. 151), in apatite glass ceramics (ibid., p. 164) or in basalt glass ceramics (ibid., p. 186).

From WO 2009/140632 (Ohio State University) lanthan oxide-doped bioactive glass ceramics which can contain diopside as a crystal phase are known as component of, for example, dental restorations.

From U.S. Pat. No. 4,560,666 (Hoya Corporation) bioactive glass ceramics are known which can contain apatite and diopside and are intended to be used as material for artificial bones or artificial dental roots. WO 2012/172316 (University of Sheffield) discloses ceramic material for dental restorations, which comprises diopside and leucite as crystal phases. EP 1 132 056 (Tokuyama Corporation) describes a process for the preparation of ceramic tooth crowns using a diopside-containing glass ceramic.

U.S. Pat. No. 4,643,982 (Hoya Corporation) describes high-strength anorthite glass ceramics, which can contain apatite or calcium phosphate crystals as well as optionally further crystal phases such as diopside. Due to the presence of several crystal phases, the glass ceramics are characterized by a high opacity. For this reason, they are not suitable for aesthetically demanding dental restorations. Rather they are intended as implant material or material for root pins for which no particular optical properties are necessary.

U.S. Pat. No. 5,066,619 (Hoya Corporation) describes glass ceramics with a mica phase and at least one further crystal phase selected from enstatite, akermanite, diopside, anorthite and richterite, which are said to be suitable for the preparation of tooth crowns. From U.S. Pat. No. 5,246,889 (Hoya Corporation) mica glass ceramics are likewise known which have zirconium oxide as further crystal phase. In some of the glass ceramics described crystal phases of enstatite, akermanite, diopside, anorthite, richterite and forsterite can also occur.

U.S. Pat. Nos. 4,871,384 and 5,232,878 (both Hoya Corporation) describe bioactive apatite glass ceramics which, among other things, can contain diopside as further crystal phase. The glass ceramics are mainly provided as bone replacement material.

U.S. Pat. Nos. 5,356,436 and 5,711,763 (both TDK Corporation) disclose ceramic materials to replace hard body tissues, which materials have wollastonite, diopside or a combination of these crystal phases.

US 2005/0079226 (Pentax Corporation) describes bioactive glass which can be used as a sintering aid for bone replacement materials and, after crystallization, can contain wollastonite and diopside crystal phases.

However, the known materials have a series of disadvantages. In many cases the translucence of these materials cannot be adjusted over a broad range as is desirable for dental materials which can be used for many purposes. Moreover, simple machining of them is often not possible. In addition, their strength often proves not to be sufficient to allow them to be used as restorative dental material.

SUMMARY OF THE INVENTION

The object of the invention is to make available a glass ceramic which has good optical properties, in particular a controllable translucence, as well as good mechanical properties and thus can be used as a restorative dental material. The glass ceramic should, moreover, be able to be processed simply and quickly using machining, e.g. using CAD/CAM processes to form dental restorations. This simple processing should, in particular, also be possible after the desired crystal phases have crystallized as completely as possible.

BRIEF DESCRIPTION OF THE DRAWINGS

Further advantages, details and features may be taken from the following description of an exemplary embodiment of the invention in conjunction with the drawings, in which.

DETAILED DESCRIPTION

Figure 1:
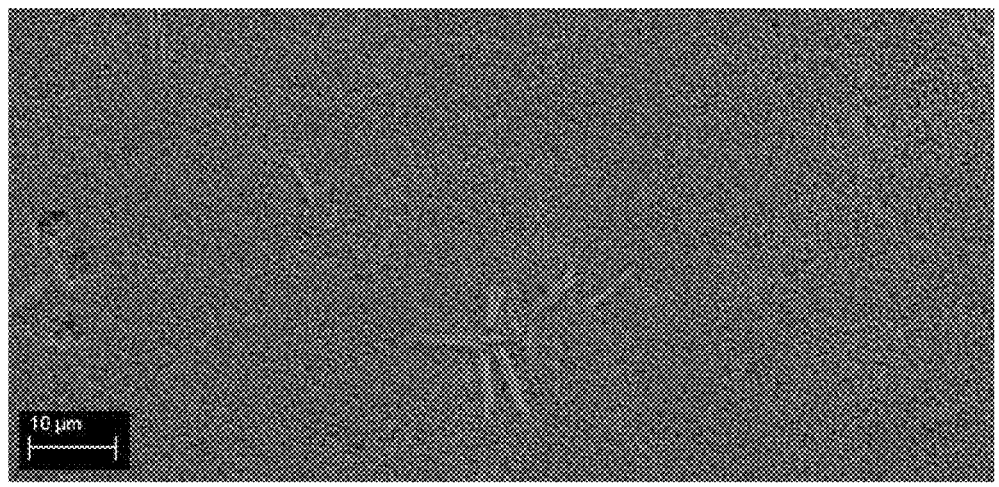
FIG. 1 shows one example of the microstructure of the glass ceramic.

This object is achieved by the lithium silicate-diopside glass ceramic which comprises lithium silicate as main crystal phase and diopside as further crystal phase. Also a subject of the invention are the starting glass for the lithium silicate-diopside glass ceramic, and the process for the preparation of the lithium silicate-diopside glass ceramic.

The lithium silicate-diopside glass ceramic according to the invention is characterized in that it comprises lithium silicate as main crystal phase and diopside as further crystal phase.

This glass ceramic surprisingly displays an advantageous combination of mechanical and optical properties desirable for a restorative dental material, and it can also be given the desired shape, for example of a dental restoration such as a crown, in a manner advantageous for a dental material.

The glass ceramic according to the invention comprises in particular 53.0 to 75.0, preferably 54.0 to 74.0 and particularly preferably 58.0 to 70.0 wt.-% $SiO_2$.

It is further preferred that the glass ceramic comprises 10.0 to 23.0, in particular 11.0 to 20.0 and particularly preferably 11.0 to 16.0 wt.-% $Li_2O$.

The molar ratio of $SiO_2$ to $Li_2O$ is in particular 2.0 to 3.0.

It is further preferred that the glass ceramic comprises 1.0 to 13.0, in particular 1.0 to 9.0 and particularly preferably 1.0 to 6.0 wt.-% CaO.

The glass ceramic preferably comprises 1.0 to 12.0, in particular 2.0 to 9.0 and particularly preferably 2.0 to 5.0 wt.-% MgO.

The molar ratio of CaO to MgO is preferably 0.5 to 2.0, particularly preferably 0.8 to 1.2 and quite particularly preferably about 1.0.

A glass ceramic is further preferred that comprises 0 to 8.0, in particular 2.0 to 6.0 and particularly preferably 3.0 to 6.0 wt.-% $P_2O_5$. $P_2O_5$ can in particular act as nucleating agent for the formation of lithium silicate. The presence of a nucleating agent is, however, not absolutely necessary for the formation of lithium silicate as main crystal phase.

It is also preferred that the glass ceramic, in addition to $Li_2O$, comprises further alkali metal oxide $Me^{I}_2O$ in an amount of from 0 to 10.0, in particular 0.5 to 8.0 and particularly preferably 1.0 to 5.0 wt.-%. The term "further alkali metal oxide $Me^{I}_2O$" denotes alkali metal oxide with the exception of $Li_2O$, wherein this $Me^{I}_2O$ is selected in particular from $Na_2O$, $K_2O$, $Rb_2O$ and/or $Cs_2O$. The glass ceramic particularly preferably comprises at least one and in particular all of the following further alkali metal oxides $Me^{I}_2O$ in the amounts specified:

| Component | wt.-% |
|---|---|
| $Na_2O$ | 0 to 3.0, in particular 0 to 2.0 |
| $K_2O$ | 0 to 5.0 |
| $Rb_2O$ | 0 to 3.0, in particular 0 to 2.0 |
| $Cs_2O$ | 0 to 10.0, in particular 0 to 8.0. |

In a particularly preferred embodiment, the glass ceramic according to the invention comprises 0.1 to 5.0 and in particular 0.5 to 4.5 wt.-% $K_2O$.

In addition it is preferred that the glass ceramic comprises 0 to 10.0 and in particular 2.0 to 7.0 wt.-% further oxide of divalent elements $Me^{II}O$. The term "further oxide of divalent elements $Me^{II}O$" denotes divalent oxides with the exception of CaO and MgO, wherein this $Me^{II}O$ is selected in particular from SrO and/or ZnO. The glass ceramic particularly preferably comprises at least one and in particular all of the following further oxides of divalent elements $Me^{II}O$ in the amounts specified:

| Component | wt.-% |
|---|---|
| SrO | 0 to 5.0 |
| ZnO | 0 to 5.0. |

Further, a glass ceramic is preferred which comprises 0 to 10.0, preferably 0 to 8.0 and in particular 2.0 to 5.0 wt.-% oxide of trivalent elements $Me^{III}_2O_3$, wherein this $Me^{III}_2O_3$ is selected in particular from $Al_2O_3$, $B_2O_3$, $Y_2O_3$, $La_2O_3$, $Ga_2O_3$ and/or $In_2O_3$. The glass ceramic particularly preferably comprises at least one and in particular all of the following oxides of trivalent elements $Me^{III}_2O_3$ in the amounts specified:

| Component | wt.-% |
|---|---|
| $Al_2O_3$ | 0 to 8.0 |
| $Y_2O_3$ | 0 to 5.0 |
| $B_2O_3$ | 0 to 4.0 |
| $Ga_2O_3$ | 0 to 5.0 |
| $In_2O_3$ | 0 to 5.0 |
| $La_2O_3$ | 0 to 5.0. |

In a particularly preferred embodiment, the glass ceramic according to the invention comprises 0.1 to 8.0, in particular 1.0 to 7.0 wt.-% and particularly preferably 2.0 to 5.0 wt.-% $Al_2O_3$.

Furthermore, a glass ceramic is preferred which comprises further oxide of tetravalent elements $Me^{IV}O_2$ in an amount of from 0 to 15.0 wt.-% and preferably 0 to 10.0 wt.-%. The term "further oxide of tetravalent elements $Me^{IV}O_2$" denotes tetravalent oxides with the exception of $SiO_2$, wherein this $Me^{IV}O_2$ is selected in particular from $ZrO_2$, $GeO_2$, $CeO_2$, $TiO_2$ and/or $SnO_2$. The glass ceramic particularly preferably comprises at least one and in particular all of the following further oxides of tetravalent elements $Me^{IV}O_2$ in the amounts specified:

| Component | wt.-% |
|---|---|
| $ZrO_2$ | 0 to 7.0 |
| $TiO_2$ | 0 to 5.0 |
| $SnO_2$ | 0 to 5.0 |
| $GeO_2$ | 0 to 14.0 |
| $CeO_2$ | 0 to 2.0. |

Moreover, a glass ceramic is preferred which comprises further oxide of pentavalent elements $Me^{V}_2O_5$ in an amount of from 0 to 4.0 and in particular 0 to 3.0 wt.-%. The term "further oxide of pentavalent elements $Me^{V}_2O_5$" denotes pentavalent oxides with the exception of $P_2O_5$, wherein this $Me^{V}_2O_5$ is selected in particular from $V_2O_5$, $Ta_2O_5$ and/or $Nb_2O_5$. The glass ceramic particularly preferably comprises at least one and in particular all of the following further oxides of pentavalent elements $Me^{V}_2O_5$ in the amounts specified:

| Component | wt.-% |
|---|---|
| $V_2O_5$ | 0 to 1.0 |
| $Ta_2O_5$ | 0 to 3.0 |
| $Nb_2O_5$ | 0 to 3.0. |

A glass ceramic is also preferred which comprises 0 to 5.0 wt.-% oxide of hexavalent elements $Me^{VI}O_3$, wherein this $Me^{VI}O_3$ is selected in particular from $WO_3$ and/or $MoO_3$. The glass ceramic particularly preferably comprises at least one and in particular all of the following oxides $Me^{VI}O_3$ in the amounts specified:

| Component | wt.-% |
|---|---|
| $WO_3$ | 0 to 5.0 |
| $MoO_3$ | 0 to 5.0. |

In addition, a glass ceramic is preferred which comprises 0 to 3.0 and in particular 0 to 1.0 wt.-% fluorine.

A glass ceramic is particularly preferred which comprises at least one and preferably all of the following components in the amounts specified:

| Component | wt.-% |
| --- | --- |
| $SiO_2$ | 53.0 to 75.0 |
| $Li_2O$ | 10.0 to 23.0 |
| CaO | 1.0 to 13.0 |
| MgO | 1.0 to 12.0 |
| $P_2O_5$ | 0 to 8.0 |
| $Me^I_2O$ | 0 to 10.0 |
| $Me^{II}O$ | 0 to 10.0 |
| $Me^{III}_2O_3$ | 0 to 10.0 |
| $Me^{IV}O_2$ | 0 to 15.0 |
| $Me^V_2O_5$ | 0 to 4.0 |
| $Me^{VI}O_3$ | 0 to 5.0 |
| fluorine | 0 to 3.0 | wherein $Me^I_2O$, $Me^{II}O$, $Me^{III}_2O_3$, $Me^{IV}O_2$, $Me^V_2O_5$ and $Me^{VI}O_3$ have the above-specified meaning.

Some of the above-named components can serve as colorants and/or fluorescent agents. The glass ceramic according to the invention can in addition also comprise further colorants and/or fluorescent agents, which can be selected in particular from inorganic pigments and/or oxides of d- and f-elements, such as the oxides of Sc, Mn, Fe, Co, Pr, Nd, Tb, Er, Dy, Gd, Eu and Yb. Metal colloids, e.g. of Ag, Au and Pd, which can in addition also act as nucleating agents, can also be used as further colorants. These metal colloids can be formed e.g. by reduction of corresponding oxides, chlorides or nitrates during the melting and crystallization processes.

The properties of the glass ceramic are essentially influenced by the crystal phases. The glass ceramic according to the invention comprises lithium silicate as main crystal phase. The term "lithium silicate" denotes at least one crystal phase selected from lithium disilicate and lithium metasilicate. Consequently, the glass ceramic according to the invention comprises lithium disilicate, lithium metasilicate or a mixture of lithium disilicate and lithium metasilicate as main crystal phase. In a preferred embodiment, the glass ceramic according to the invention comprises lithium disilicate as main crystal phase.

The term "main crystal phase" refers to the crystal phase which has the highest proportion by mass of all the crystal phases present in the glass ceramic. The masses of the crystal phases are determined in particular using the Rietveld method. A suitable process for the quantitative analysis of the crystal phases using the Rietveld method is described e.g. in M. Dittmer's doctoral thesis "Gläser and Glaskeramiken im System MgO—$Al_2O_3$—$SiO_2$ mit $ZrO_2$ als Keimbildner" [Glasses and glass ceramics in the MgO—$Al_2O_3$—$SiO_2$ system with $ZrO_2$ as nucleating agent], University of Jena 2011.

It is further preferred that the glass ceramic according to the invention comprises 10.0 to 75.0 and in particular 20.0 to 75.0 wt.-% lithium silicate as crystal phase. In particular it is preferred that the glass ceramic comprises 20.0 to 75.0 and in particular 25.0 to 60.0 wt.-% lithium disilicate and/or 10.0 to 60.0 and in particular 20.0 to 50.0 wt.-% lithium metasilicate as crystal phase.

The glass ceramic according to the invention also comprises, in addition to lithium silicate as main crystal phase, diopside as further crystal phase. In a preferred embodiment, the glass ceramic comprises 0.1 to 50.0, in particular 0.1 to 25.0, particularly preferably 0.1 to 7.0 and quite particularly preferably 0.1 to 5.0 wt.-% diopside.

The glass ceramic according to the invention can furthermore comprise further crystal phases, such as for example $Li_3PO_4$, $SiO_2$ modifications, enstatite and/or $Cs_{0.809}AlSi_5O_{12}$.

The type and quantity of crystal phases formed can be controlled in particular by the composition of the starting glass as well as the process for the preparation of the glass ceramic. The examples illustrate this by means of the variation of the composition and the preparation process.

It was surprisingly found that a glass ceramic can be provided which, in addition to a diopside crystal phase, also has a lithium silicate crystal phase. In particular it could not be foreseen that such a glass ceramic can be formed in the preferred composition range described above. It was found that the nucleation and the growth of both crystal phases obviously proceed alongside one another in the starting glass. Therefore, lithium silicate crystals could be detected in the volume of the starting glass while diopside crystals could be detected on the surface of the starting glass. Accordingly, nucleation and growth of lithium silicate crystals seems to occur in the volume of the starting glass while, in contrast, nucleation and growth of diopside crystals seems to occur on the surface of the starting glass. Among experts, crystallization in the volume of a glass is also called volume crystallization and a crystallization on the surface is also called surface crystallization.

However, nucleation and crystallization on the surface does not take place readily during the preparation of the glass ceramic according to the invention. Rather it was found that it is necessary to activate the surface of the starting glass by grinding it. By means of this specific activation a reproducible surface crystallization of diopside is achieved. The grinding method, for example the use of different mills, can influence the final amount of crystallized diopside.

The amount of diopside in the glass ceramic according to the invention is thus not determined, for example, by the MgO and CaO content in the starting glass or the heat treatment thereof but also by the method of the activation due to the grinding of the starting glass.

In addition it was found that the amount of precipitated diopside has an influence on the translucence of the glass ceramic according to the invention. By means of a diopside content of in particular more than 5.0 wt.-%, strongly opaque glass ceramics with a contrast value (CR value according to British Standard BS 5612) of more than 90 can be produced. These glass ceramics are particularly suitable for the preparation of a dental abutment structure or a dental framework onto which a suitable veneer is applied.

By means of a relatively small diopside content of in particular less than 5.0 and preferably less than 2.0 wt.-%, translucent glass ceramics with a CR value of less than 75 can be produced. These glass ceramics are suitable in particular for the preparation of optically demanding dental restorations, such as crowns, veneers and inlays.

The glass ceramic according to the invention is further characterized in that, even after the formation of the lithium disilicate crystal phase has finished, which gives the glass ceramic a high strength, it can be easily processed by machining in order to give it e.g. the shape of a dental restoration. This is a particular advantage vis-à-vis conventional lithium disilicate glass ceramics, in the case of which a precursor which can be machined more easily is often used and this precursor must then be subjected to a heat treatment after the machining to form the desired lithium disilicate glass ceramic.

The glass ceramic according to the invention is also characterized by a very good chemical resistance. To determine the chemical resistance, the glass ceramic was tested according to ISO standard 6872 (2008) by determining the mass loss during storage in aqueous acetic acid. The glass ceramic according to the invention displayed a mass loss of preferably less than 100 µg/cm².

The glass ceramic according to the invention also has a biaxial breaking strength $\sigma_B$ of preferably at least 200 MPa and particularly preferably 200 to 400 MPa. The biaxial breaking strength was determined according to ISO 6872 (2008) (piston-on-three-ball test).

Therefore, the glass ceramic according to the invention offers a desirable combination of advantageous optical and mechanical properties as are sought in particular for a dental material.

The invention likewise relates to precursors with a corresponding composition from which the glass ceramic according to the invention can be prepared by heat treatment. These precursors are a starting glass with a corresponding composition and a starting glass with nuclei with a corresponding composition. The designation "corresponding composition" means that these precursors comprise the same components in the same amounts as the glass ceramic, the components with the exception of fluorine are being calculated as oxides, as is customary for glasses and glass ceramics.

The invention therefore also relates to a starting glass which comprises the components of the lithium silicate-diopside glass ceramic according to the invention. All those embodiments which are also specified as preferred for the components of the lithium silicate-diopside glass ceramic according to the invention are preferred for the components of the starting glass.

Particularly preferably the starting glass is present in ground form or in the form of a powder green compact pressed from ground starting glass. In both of these forms the starting glass has experienced an activation by means of the grinding, which activation is required for the later crystallization of diopside.

The invention also relates further to a starting glass which comprises nuclei for the crystallization of lithium silicate and/or diopside.

The invention further relates to a process for the preparation of the lithium silicate-diopside glass ceramic according to the invention, in which
(a) starting glass is ground,
(b) the ground starting glass is optionally pressed to form a powder green compact and
(c) the ground starting glass or the powder green compact is subjected to at least one heat treatment at a temperature in the range of from 500° to 1000° C. for a period of from 5 to 120 min.

In step (a) the starting glass according to the invention is ground in order to activate it for the crystallization of diopside.

The grinding is carried out in particular in mills and preferably in ball mills, jet mills, such as opposed jet mills, or vibratory mills. The glass particles obtained after the grinding generally have an average particle size in the range of from 100 nm to 100 µm, relative to the number of particles.

By using different grinding processes, e.g. by using different mills, different degrees of activation of the starting glass can be achieved and thus also the amount of diopside finally crystallized can be controlled.

The starting glass subjected to the grinding process is preferably present in the form of a granular material. The term "granular material" denotes a particulate starting glass. To produce particulate starting glass a melt of the starting glass can be poured into water and thus quenched. This process is also called fritting and the glass granules obtained are called glass frits. A granular material can, however, also be produced in another way, such as for example by quenching in a roller mill with subsequent comminution.

The preparation of the starting glass is carried out in particular in that a mixture of suitable starting materials, such as carbonates, oxides and phosphates, is melted at temperatures of in particular 1300 to 1700° C., preferably at about 1500° C., for a period of from 0.5 to 5 h.

In the optional step (b) the ground starting glass is pressed to form a powder green compact. It is preferred that this step is carried out in the process according to the invention.

In contrast to a glass monolith, as is obtained e.g. by pouring a glass melt into a mould, the powder green compact according to the invention is characterized by a high inner surface on which crystallization of diopside can take place.

The powder green compact can have any desired geometry. Typically, the powder green compact already has essentially the shape intended for a blank which is made from the later produced glass ceramic according to the invention.

In step (c) the ground glass or the powder green compact is subjected to at least one heat treatment. This at least one heat treatment takes place at a temperature in the range of from 500° to 1000° C., preferably 700° to 1000° C., preferably 750° to 950° C. and particularly preferably 800° to 950° C. for a period of from 5 to 120 min, preferably 5 to 90 min.

The heat treatment is carried out until the desired amount of lithium silicate and diopside is crystallized and thus the lithium silicate-diopside glass ceramic according to the invention has been formed. The heat treatment can also take place in stages, wherein first of all a precursor, such as a nucleated starting glass, is formed by means of a first heat treatment, and then the glass ceramic according to the invention is formed by means of a second heat treatment at a higher temperature. The formation of nuclei for the crystallization of lithium silicate usually takes place at a temperature in the range of from 450 to 600° C.

It is further preferred to choose the heat treatment such that there is also at least a partial sintering, i.e. a pre-sintering of the ground starting glass or of the powder green compact. It is particularly preferred when the heat treatment also leads to as complete a sintering as possible, i.e. to a dense sintering of the ground starting glass or of the powder green compact.

Densely-sintered glass ceramics produced from ground starting glass are used above all as coatings on substrates such as dental framework. Densely-sintered glass ceramics produced from powder green compacts are used above all as blanks from which dental restorations such as bridges, crowns, inlays or onlays can be prepared using suitable shaping processes such as pressing and in particular machining.

After step (c) has finished, the lithium silicate-diopside glass ceramic according to the invention is present.

Dental restorations, such as bridges, inlays, onlays, crowns, veneers, shells or abutments, can be prepared from the glass ceramic according to the invention and the glasses according to the invention. The invention therefore relates to the use thereof as dental material and in particular to the use thereof for the preparation of dental restorations. It is preferred that the glass ceramic or the glass is given the shape of the desired dental restoration by pressing or machining.

The pressing is usually carried out under increased pressure and at increased temperature. It is preferred that the pressing is carried out at a temperature of from 700 to 1200° C. It is further preferred to carry out the pressing at a pressure of from 10 to 30 bar. During pressing, the desired change in shape is achieved by viscous flow of the material used. The glasses and glass ceramics according to the invention can in particular be used in the form of blanks in any shape and size. For the pressing, the glass ceramic according to the invention is preferably used.

The machining is usually carried out by material removal processes and in particular by milling and/or grinding. It is particularly preferred that the machining is carried out as part of a CAD/CAM process. The glasses and glass ceramics according to the invention can be used in particular in the form of blanks. These are regularly adapted to the type of machine used for the machining in terms of their shape. The glass ceramic according to the invention is in particular used for the machining.

Because of the above-described properties of the glass ceramics according to the invention and the glasses according to the invention, these are suitable in particular for use in dentistry. The subject-matter of the invention is therefore also the use of the glass ceramics according to the invention or the glasses according to the invention as dental material and in particular for the preparation of dental restorations such as crowns, bridges and abutments.

The invention therefore also relates to a process for the preparation of a dental restoration, in particular bridge, inlay, onlay, veneer, abutment, partial crown, crown or shell, in which the glass ceramic according to the invention or the glass according to the invention is given the shape of the desired dental restoration by pressing or by machining, in particular as part of a CAD/CAM process.

The invention further relates to a process for coating a substrate in which ground starting glass is applied to the substrate and crystallized as well as sintered. The crystallization and sintering takes place under the conditions as are specified above for the heat treatment according to step (c) of the process according to the invention. As substrates, in particular oxide ceramics or glass ceramics are useful. Suitable oxide ceramics are $Al_2O_3$ or $ZrO_2$ ceramics as well as mixtures thereof, e.g. partially or completely stabilized $ZrO_2$ ceramic with MgO, CaO, $Y_2O_3$ and/or $CeO_2$ contents. Suitable glass ceramics are lithium silicate glass ceramics or glass ceramics of the $SiO_2$—$Al_2O_3$—$K_2O$ type.

The invention is described in more detail below with reference to non-limiting examples.

EXAMPLES

Examples 1 to 22—Composition and Crystal Phases

In total, 22 glasses and glass ceramics with the composition specified in Table I were prepared.

The following meanings apply in Table I:

| | |
|---|---|
| $T_g$ | glass transition temperature, determined by means of DSC |
| $T_S$ and $t_S$ | temperature and time used for melting the starting glass |
| $T_{Sinter}$ and $t_{Sinter}$ | temperature and time used for the heat treatment and thus crystallization of compacts |
| $T_{Press}$ and $t_{Press}$ | temperature and time used for pressing crystallized compacts |
| L*a*b value | key for characterizing the colour |
| CR value | contrast value of the glass ceramic according to British Standard BS 5612 |
| $Li_2Si_2O_5$ | lithium disilicate |
| $Li_2SiO_3$ | lithium metasilicate |
| $CaMgSi_2O_6$ | diopside |
| $SiO_2$ | quartz, in particular low quartz, or cristobalite |
| $Cs_{0.809}AlSi_5O_{12}$ | caesium alumosilicate |

In Examples 1 to 22 glasses from usual raw materials were melted in a platinum crucible at the temperature $T_S$ for a period $t_S$. Glass frits, i.e. glass granules, were prepared by pouring the melted starting glasses into water. For the further processing of the glass frits, the three process variants A), B) and C) specified below were used:

A) Vibratory Mills

The glass frits prepared according to Examples 1 to 9, 11 to 19, 21 and 22 were ground with a KM100 vibratory mill from Retsch GmbH, Haan, Germany, and an RM31 zirconium oxide vibratory mill from Retsch GmbH, Haan, Germany to an average particle size of <90 μm, relative to the number of particles. The ground glass powder was then pressed uniaxially to form a small cylinder and crystallized and sintered in a Programat-type furnace (Ivoclar Vivadent AG) at the temperature $T_{Sinter}$ for the period $t_{Sinter}$. X-ray diffraction analyses were carried out on the test pieces prepared to determine the crystal phases present and colour measurements were also carried out.

B) Jet Mill

The glass frit with the composition according to Example 10 was ground in an AFG 100 opposed jet mill from Hosokawa Alpine to an average particle size of 20 μm, relative to the number of particles. The ground glass powder was then pressed uniaxially and crystallized and sintered in a Programat-type furnace (Ivoclar Vivadent AG) at the temperature $T_{Sinter}$ for the period $t_{Sinter}$. Colour measurements and X-ray diffraction analyses were carried out on the test pieces prepared in this way. The CR value of the lithium silicate-diopside glass ceramic produced was 69.95.

C) Ball Mill

The glass frit with the composition according to Example 20 was ground in a ball mill for a period of about 20 h to an average particle size of 10 μm, relative to the number of particles. The ball mill had, as grinding chamber, a cylindrical porcelain container with a volumetric capacity of 1. The following mixture of porcelain grinding balls was used as grinding medium: 0.9 kg with 10 mm diameter, 1.8 kg with 20 mm diameter and 0.9 kg with 30 mm diameter. The ground glass powder was then pressed uniaxially and crystallized and sintered in a Programat-type furnace (Ivoclar Vivadent AG) at the temperature $T_{Sinter}$ for the period $t_{Sinter}$. Colour measurements and X-ray diffraction analyses were carried out on the test pieces prepared in this way to determine the crystal phases. The content of diopside crystals in this glass ceramic was higher than in the glass ceramics prepared according to variants A) and B).

TABLE I

| | Example No. | | | | | |
|---|---|---|---|---|---|---|
| | 1 | 2 | 3 | 4 | 5 | 6 |
| Composition | wt.-% | wt.-% | wt.-% | wt.-% | wt.-% | wt.-% |
| $SiO_2$ | 67.1 | 60.9 | 68.5 | 61.1 | 67.6 | 66.9 |
| $Li_2O$ | 14.0 | 21.7 | 14.2 | 14.3 | 14.0 | 13.8 |

TABLE I-continued

| | | | | | | |
|---|---|---|---|---|---|---|
| CaO | 5.2 | 8.7 | 4.2 | 5.1 | 4.1 | 3.9 |
| MgO | 3.8 | 8.7 | 3.0 | 3.7 | 3.0 | 2.8 |
| $Na_2O$ | — | — | — | — | — | — |
| $K_2O$ | 3.6 | — | 3.7 | 3.4 | 3.3 | 3.4 |
| $Cs_2O$ | — | — | — | — | — | — |
| $Rb_2O$ | — | — | — | — | 1.7 | — |
| ZnO | — | — | — | — | — | — |
| SrO | — | — | — | — | — | — |
| $Al_2O_3$ | 3.2 | — | 3.3 | 3.1 | 3.2 | 4.0 |
| $B_2O_3$ | — | — | — | — | — | — |
| $Y_2O_3$ | — | — | — | — | — | — |
| $La_2O_3$ | — | — | — | — | — | — |
| $Er_2O_3$ | — | — | — | — | — | — |
| $ZrO_2$ | — | — | — | 5.9 | — | — |
| $CeO_2$ | — | — | — | — | — | — |
| $P_2O_5$ | 3.1 | — | 3.1 | 3.4 | 3.1 | 5.2 |
| $V_2O_5$ | — | — | — | — | — | — |
| $Nb_2O_5$ | — | — | — | — | — | — |
| $WO_3$ | — | — | — | — | — | — |
| F | — | — | — | — | — | — |
| $GeO_2$ | — | — | — | — | — | — |
| $T_g$/° C. | 456.9 | | 454.2 | | 455.2 | 462.6 |
| $T_s$/° C., $t_s$/min | 1500, 120 | | 1500, 120 | 1500, 120 | 1500, 120 | 1500, 150 |
| $T_{Sinter}$/° C., $t_{Sinter}$/min | 800, 5 | 930, 10 | 780, 8 | 800, 8 | 840, 5 | 830, 5 |
| $T_{Press}$/° C., $t_{Press}$/° C. | 910, 25 | | | | | |
| Main crystal phase | $Li_2Si_2O_5$ (Sinter) $Li_2SiO_3$ (Sinter and press) | $Li_2Si_2O_5$ | $Li_2Si_2O_5$ | $Li_2SiO_3$ | $Li_2Si_2O_5$ | $Li_2Si_2O_5$ |
| Further crystal phases | $CaMgSi_2O_6$, $Li_2SiO_3$, $Li_3PO_4$, $SiO_2$ | $CaMgSi_2O_6$, $SiO_2$ | $CaMgSi_2O_6$, $Li_2SiO_3$, $Li_3PO_4$ | $CaMgSi_2O_6$, $Li_3PO_4$ | $CaMgSi_2O_6$, $Li_2SiO_3$, $Li_3PO_4$ | $CaMgSi_2O_6$, $Li_3PO_4$, quartz, low cristobalite |
| L* | | | | | | 87.8 |
| a* | | | | | | 0.58 |
| b* | | | | | | 4.78 |
| CR | | | | | | 88.6 |

| | Example No. | | | | | |
|---|---|---|---|---|---|---|
| Composition | 7 wt.-% | 8 wt.-% | 9 wt.-% | 10 wt.-% | 11 wt.-% | 12 wt.-% |
| $SiO_2$ | 65.8 | 73.2 | 65.7 | 66.7 | 58.0 | 67.9 |
| $Li_2O$ | 11.8 | 13.6 | 13.3 | 13.8 | 19.6 | 14.0 |
| CaO | 4.0 | 4.2 | 4.0 | 4.0 | 5.4 | 3.7 |
| MgO | 2.9 | 3.0 | 2.9 | 2.9 | 3.9 | 4.5 |
| $Na_2O$ | — | — | — | — | — | — |
| $K_2O$ | 3.7 | 0.9 | 3.2 | 3.4 | 4.2 | 3.6 |
| $Cs_2O$ | — | — | — | — | — | — |
| $Rb_2O$ | — | — | — | — | — | — |
| ZnO | — | — | — | — | — | — |
| SrO | — | — | — | — | — | — |
| $Al_2O_3$ | 3.6 | 1.9 | 3.2 | 4.0 | 3.4 | 3.2 |
| $B_2O_3$ | 3.1 | — | — | — | — | — |
| $Y_2O_3$ | — | — | — | — | — | — |
| $La_2O_3$ | — | — | — | — | — | — |
| $Er_2O_3$ | — | — | — | — | — | — |
| $ZrO_2$ | — | — | — | — | — | — |
| $CeO_2$ | — | — | — | — | — | — |
| $P_2O_5$ | 5.1 | 3.2 | 7.7 | 5.2 | 5.5 | 3.1 |
| $V_2O_5$ | — | — | — | — | — | — |
| $Nb_2O_5$ | — | — | — | — | — | — |
| $WO_3$ | — | — | — | — | — | — |
| F | — | — | — | — | — | — |
| $GeO_2$ | — | — | — | — | — | — |
| $T_g$/° C. | 459.9 | 460.3 | 470.3 | 463.4 | | 453 |
| $T_s$/° C., $t_s$/min | 1500, 150 | 1500, 60 | 1500, 120 | 1400, 240 | 1500, 120 | 1500, 120 |
| $T_{Sinter}$/° C., $t_{Sinter}$/min | 800, 5 | 800, 5 | 840, 5 | 820, 5 | 900, 5 | 800, 5 |
| $T_{Press}$/° C., $t_{Press}$/° C. | | | | | | |
| Main crystal phase | $Li_2Si_2O_5$ | $Li_2Si_2O_5$ | $Li_2Si_2O_5$ | $Li_2Si_2O_5$ | $Li_2SiO_3$ | $Li_2Si_2O_5$ |
| Further crystal phases | $CaMgSi_2O_6$, $Li_3PO_4$, quartz | $CaMgSi_2O_6$, $Li_3PO_4$, quartz, low cristobalite | $CaMgSi_2O_6$, low quartz, $Li_3PO_4$ | $CaMgSi_2O_6$, $Li_3PO_4$, $MgSiO_3$ | $CaMgSi_2O_6$, $Li_2Si_2O_5$, $Li_3PO_4$ | $CaMgSi_2O_6$, $Li_2SiO_3$, $Li_3PO_4$ |
| L* | 85.5 | 85.97 | 92.07 | 89.53 | 85.5 | |
| a* | 0.71 | 0.38 | −0.24 | 0.71 | 0.37 | |

TABLE I-continued

| | | | | | |
|---|---|---|---|---|---|
| b* | 6.9 | 4.95 | 4.09 | 5.59 | 5.36 |
| CR | 84.72 | 89.69 | 69.95 | 93.81 | 84.97 |

| | Example No. | | | | | |
|---|---|---|---|---|---|---|
| Composition | 13 wt.-% | 14 wt.-% | 15 wt.-% | 16 wt.-% | 17 wt.-% | 18 wt.-% |
| $SiO_2$ | 65.6 | 64.3 | 67.6 | 54.7 | 65.5 | 62.8 |
| $Li_2O$ | 13.8 | 13.3 | 14.0 | 11.2 | 13.9 | 13.0 |
| CaO | 4.9 | 4.9 | 4.1 | 5.3 | 4.7 | 4.5 |
| MgO | 3.5 | 3.5 | 3.0 | 3.8 | 3.4 | 3.2 |
| $Na_2O$ | — | — | — | — | — | — |
| $K_2O$ | 3.1 | 2.5 | 3.7 | 3.5 | 3.4 | 0.7 |
| $Cs_2O$ | — | — | — | — | — | 7.5 |
| $Rb_2O$ | — | — | — | — | — | — |
| ZnO | — | — | — | — | — | — |
| SrO | — | 4.7 | — | — | — | — |
| $Al_2O_3$ | 2.6 | 2.8 | 3.2 | 3.3 | 2.7 | 3.4 |
| $B_2O_3$ | — | — | — | — | — | — |
| $Y_2O_3$ | — | — | — | — | — | — |
| $La_2O_3$ | — | — | — | — | — | — |
| $Er_2O_3$ | — | — | 0.4 | — | — | — |
| $ZrO_2$ | — | — | — | — | — | — |
| $CeO_2$ | — | — | 0.8 | — | — | — |
| $P_2O_5$ | 4.0 | 4.0 | 3.1 | 4.8 | 4.0 | 4.9 |
| $V_2O_5$ | — | — | 0.1 | — | — | — |
| $Nb_2O_5$ | — | — | — | — | 2.4 | — |
| $WO_3$ | 2.5 | — | — | — | — | — |
| F | — | — | — | — | — | — |
| $GeO_2$ | — | — | — | 13.4 | — | — |
| $T_g$/° C. | 460.7 | 453.9 | 452.2 | 462.2 | | 465.2 |
| $T_s$/° C., $t_s$/min | 1500, 120 | 1500, 120 | 1500, 120 | 1500, 120 | 1500, 120 | 1500, 120 |
| $T_{Sinter}$/° C., $t_{Sinter}$/min | 800, 5P11 | 800, 5 | 850, 10 | 730, 5 | 800, 5 | 810, 5 |
| $T_{Press}$/° C., $t_{Press}$/° C. | | | | | | |
| Main crystal phase | $Li_2Si_2O_5$ | $Li_2Si_2O_5$ | $Li_2Si_2O_5$ | $Li_2Si_2O_5$/$Li_2SiO_3$ | $Li_2Si_2O_5$ | $Li_2Si_2O_5$ |
| Further crystal phases | $CaMgSi_2O_6$, $Li_3PO_4$ | $CaMgSi_2O_6$, $Li_2SiO_3$, $Li_3PO_4$ | $CaMgSi_2O_6$, $Li_2SiO_3$ $Li_3PO_4$ | $CaMgSi_2O_6$, $Li_3SiO_4$ | $CaMgSi_2O_6$, $Li_2SiO_3$ $Li_3PO_4$ | $CaMgSi_2O_6$, $Li_3PO_4$, $Cs_{0.809}AlSi_5O_{12}$ |
| L* | 83.09 | | 86.84 | 78.76 | 81.47 | 80.42 |
| a* | −0.35 | | 0.23 | 0.61 | 0.78 | 0.57 |
| b* | 0.96 | | 4.39 | 6.56 | 9.77 | 3.59 |
| CR | 99.96 | | 96.22 | 84.81 | 88.96 | 99.82 |

| | Example No. | | | |
|---|---|---|---|---|
| Composition | 19 wt.-% | 20 wt.-% | 21 wt.-% | 22 wt.-% |
| $SiO_2$ | 65.7 | 67.9 | 64.7 | 67.0 |
| $Li_2O$ | 13.7 | 14.0 | 13.2 | 13.9 |
| CaO | 5.1 | 3.1 | 4.5 | 6.3 |
| MgO | 3.6 | 2.2 | 3.3 | 3.0 |
| $Na_2O$ | — | — | 1.8 | — |
| $K_2O$ | 3.1 | 3.5 | 0.7 | 3.6 |
| $Cs_2O$ | — | — | — | — |
| $Rb_2O$ | — | — | — | — |
| ZnO | — | — | — | — |
| SrO | — | — | — | — |
| $Al_2O_3$ | 3.4 | 4.0 | 2.9 | 3.2 |
| $B_2O_3$ | — | — | — | — |
| $Y_2O_3$ | — | — | 4.1 | — |
| $La_2O_3$ | 1.2 | — | — | — |
| $Er_2O_3$ | — | — | — | — |
| $ZrO_2$ | — | — | — | — |
| $CeO_2$ | — | — | — | — |
| $P_2O_5$ | 4.0 | 5.3 | 4.8 | 3.0 |
| $V_2O_5$ | — | — | — | — |
| $Nb_2O_5$ | — | — | — | — |
| $WO_3$ | — | — | — | — |
| F | 0.2 | — | — | — |
| $GeO_2$ | — | — | — | — |
| $T_g$/° C. | 455.1 | 469.4 | 458.1 | 457 |
| $T_s$/° C., $t_s$/min | 1500, 120 | 1400, 240 | 1500, 120 | 1400, 120 |
| $T_{Sinter}$/° C., $t_{Sinter}$/min | 800, 5 | 860, 10 | 800, 5 | 800, 5 |
| $T_{Press}$/° C., $t_{Press}$/° C. | | | | |

TABLE I-continued

| Main crystal phase | $Li_2Si_2O_5$ | $Li_2Si_2O_5$ | $Li_2Si_2O_5$ | $Li_2Si_2O_5$ |
|---|---|---|---|---|
| Further crystal phases | $CaMgSi_2O_6$, $Li_2SiO_3$, $Li_3PO_4$ | $CaMgSi_2O_6$, cristobalite, $Li_3PO_4$ | $CaMgSi_2O_6$, $Li_3PO_4$ | $CaMgSi_2O_6$, $Li_2SiO_3$, $Li_3PO_4$ |
| L* | 79.74 | 94.92 | | 83.46 |
| a* | 0.7 | −0.3 | | 0.36 |
| b* | 5.48 | 1.5 | | 4 |
| CR | 94.56 | 85.55 | | 94.74 |

Example 23—Influence of Comminution

A glass frit with the composition according to Example 10 was ground with a ball mill in the same way as specified for Example 20 to an average particle size of 20 μm, relative to the number of particles. The ground glass powder was then pressed uniaxially and crystallized and sintered in a Programat-type furnace (Ivoclar Vivadent AG) at a temperature of 870° C. for a period of 5 min. A colour measurement (Minolta apparatus) and an X-ray diffraction analysis to determine the crystal phases were then carried out on the test piece prepared in this way. $Li_2Si_2O_5$ formed the main crystal phase of the glass ceramic. Diopside and $Li_3PO_4$ were the secondary crystal phases. The diopside content was greater than in Example 10. The increased proportion of diopside leads to a higher degree of opacity which could be read from a CR value of 90.00 instead of 69.95.

Example 24—Hot Pressing

A glass with the composition according to Example 1 was melted in a platinum crucible at a temperature of 1500° C. and then poured into water. The glass frit prepared in this way was ground with a KM100 vibratory mill from Retsch GmbH, Haan, Germany, to an average particle size of <90 μm, relative to the number of particles. A powder green compact was prepared by uniaxial pressing from the glass powder obtained. The powder green compact was crystallized and densely sintered at a temperature of 800° C. and with a holding time of 5 min in a Programat-type furnace. The crystallized and densely sintered blank was then pressed by means of hot pressing with a holding time of 25 min at a temperature of 910° C. An X-ray structural analysis was carried out on the pressed test pieces and the coefficient of thermal expansion as well as the biaxial strength of the pressed material was determined according to ISO 6872. The biaxial strength was 230 MPa.

Machinability

To test the machinability, glass powders according to Examples 3, 7, 10, 12, 16, 18 and 23 were pressed uniaxially to form blocks and densely sintered in a Programat-type furnace. Corresponding holders were then adhesively bonded to the glass ceramic blocks prepared in this way and they were processed with a CAD/CAM grinding unit (Sirona InLab). To test the processability, biaxial test pieces were ground out of the blocks.

Figure 2:
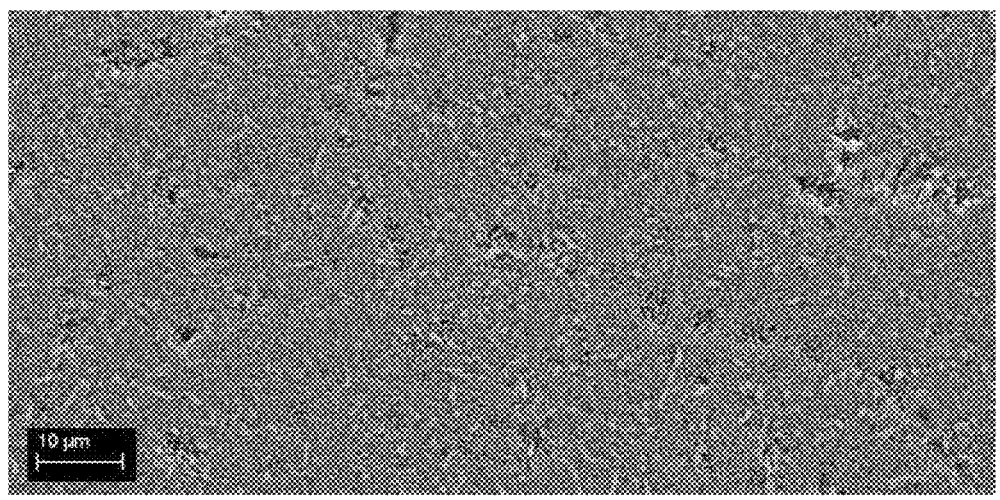
FIG. 2 shows another example of the microstructure of the glass ceramic.

FIGS. 1 and 2—Microstructure Images

FIG. 1 shows the microstructure of the glass ceramic according to Example 10. Characteristic is the very fine lithium disilicate microstructure with few interjacent diopside crystals. FIG. 2 shows the microstructure of the glass ceramic obtained according to Example 23 and the increased formation of diopside vis-à-vis Example 10 is clearly recognizable.

The invention claimed is:

1. Lithium silicate-diopside glass ceramic which comprises 2.0 to 8.0 wt.-% $P_2O_5$ and comprises lithium silicate as main crystal phase and diopside as further crystal phase.

2. Glass ceramic according to claim 1, which comprises 53.0 to 75.0 wt.-% $SiO_2$.

3. Glass ceramic according to claim 1, which comprises 10.0 to 23.0 wt.-% $Li_2O$.

4. Glass ceramic according to claim 1, which comprises 1.0 to 13.0 wt.-% CaO and/or 1.0 to 12.0 wt.-% MgO.

5. Glass ceramic according to claim 4, wherein the molar ratio of CaO to MgO is 0.5 to 2.0.

6. Glass ceramic according to claim 1, which comprises 0 to 10.0 wt.-% further alkali metal oxide $Me^I_2O$, wherein $Me^I_2O$ is selected from $Na_2O$, $K_2O$, $Rb_2O$ and/or $Cs_2O$.

7. Glass ceramic according to claim 1, which comprises 0 to 10.0 wt.-% oxide of trivalent elements $Me^{III}_2O_3$, wherein $Me^{III}_2O_3$ is selected from $Al_2O_3$, $B_2O_3$, $Y_2O_3$, $La_2O_3$, $Ga_2O_3$ and/or $In_2O_3$.

8. Glass ceramic according to claim 1, which comprises the following components:

| Component | wt.-% |
|---|---|
| $SiO_2$ | 53.0 to 75.0 |
| $Li_2O$ | 10.0 to 23.0 |
| CaO | 1.0 to 13.0 |
| MgO | 1.0 to 12.0 |
| $P_2O_5$ | 2.0 to 8.0 |
| $Me^I_2O$ | 0 to 10.0 |
| $Me^{II}O$ | 0 to 10.0 |
| $Me^{III}_2O_3$ | 0 to 10.0 |
| $Me^{IV}O_2$ | 0 to 15.0 |
| $Me^V_2O_5$ | 0 to 4.0 |
| $Me^{VI}O_3$ | 0 to 5.0 |
| fluorine | 0 to 3.0, | wherein
$Me^I_2O$ is selected from $Na_2O$, $K_2O$, $Rb_2O$ and/or $Cs_2O$,
$Me^{II}O$ is selected from SrO and/or ZnO,
$Me^{III}_2O_3$ is selected from $Al_2O_3$, $B_2O_3$, $Y_2O_3$, $La_2O_3$, $Ga_2O_3$ and/or $In_2O_3$,
$Me^{IV}O_2$ is selected from $ZrO_2$, $GeO_2$, $CeO_2$, $TiO_2$ and/or $SnO_2$,
$Me^V_2O_5$ is selected from $V_2O_5$, $Ta_2O_5$ and/or $Nb_2O_5$, and
$Me^{VI}O_3$ is $WO_3$ and/or $MoO_3$.

9. Glass ceramic according to claim 1, which comprises lithium silicate in the form of lithium disilicate and/or lithium metasilicate.

10. Glass ceramic according to claim 1, which is present in the form of a blank or a dental restoration.

11. Glass ceramic according to claim 1, which comprises 3.0 to 6.0 wt.-% $P_2O_5$.

12. Starting glass which comprises the following components:

| Component | wt.-% |
|---|---|
| $SiO_2$ | 53.0 to 75.0 |
| $Li_2O$ | 10.0 to 23.0 |
| CaO | 1.0 to 13.0 |

-continued

| Component | wt.-% |
|---|---|
| MgO | 1.0 to 12.0 |
| $Al_2O_3$ | 0.1 to 8.0 |
| $P_2O_5$ | 0 to 8.0 |
| $Me^I_2O$ | 0 to 10.0 |
| $Me^{II}O$ | 0 to 10.0 |
| $Me^{III}_2O_3$ | 0.1 to 10.0 |
| $Me^{IV}O_2$ | 0 to 15.0 |
| $Me^V_2O_5$ | 0 to 4.0 |
| $Me^{VI}O_3$ | 0 to 5.0 |
| fluorine | 0 to 3.0, | wherein $Me^I_2O$ is selected from $Na_2O$, $K_2O$, $Rb_2O$ and/or $Cs_2O$, $Me^{II}O$ is selected from SrO and/or ZnO, $Me^{III}_2O_3$ is selected from $Al_2O_3$, $B_2O_3$, $Y_2O_3$, $La_2O_3$, $Ga_2O_3$ and/or $In_2O_3$, $Me^{IV}O_2$ is selected from $ZrO_2$, $GeO_2$, $CeO_2$, $TiO_2$ and/or $SnO_2$, $Me^V_2O_5$ is selected from $V_2O_5$, $Ta_2O_5$ and/or $Nb_2O_5$, and $Me^{VI}O_3$ is $WO_3$ and/or $MoO_3$, and comprises nuclei for the crystallization of lithium metasilicate or lithium disilicate as main crystal phase and diopside as further crystal phase.

13. Starting glass according to claim 12, which is present in the form of a ground powder or a compact made of ground powder.

14. Process for the preparation of a lithium silicate-diopside glass ceramic which comprises lithium silicate as main crystal phase and diopside as further crystal phase, wherein (a) a starting glass is ground, (b) the ground starting glass is optionally pressed to form a powder green compact and (c) the ground starting glass or the powder green compact is subjected to at least one heat treatment at a temperature in the range of from 500° to 1000° C. for a period of from 5 to 120 min.

15. Lithium silicate-diopside glass ceramic, which comprises 53.0 to 70.0 wt.-% $SiO_2$ and comprises lithium silicate as main crystal phase and diopside as further crystal phase.

16. Lithium silicate-diopside glass ceramic, which comprises 0.5 to 10.0 wt.-% further alkali metal oxide $Me^I_2O$, wherein $Me^I_2O$ is selected from $Na_2O$, $K_2O$, $Rb_2O$ and/or $Cs_2O$ and comprises lithium silicate as main crystal phase and diopside as further crystal phase.

17. Glass ceramic according to claim 16, which comprises 0.5 to 8.0 further alkali metal oxide $Me^I_2O$, wherein $Me^I_2O$ is selected from $Na_2O$, $K_2O$, $Rb_2O$ and/or $Cs_2O$.

18. Glass ceramic according to claim 16, which comprises 1.0 to 5.0 wt.-% further alkali metal oxide $Me^I_2O$, wherein $Me^I_2O$ is selected from $Na_2O$, $K_2O$, $Rb_2O$ and/or $Cs_2O$.

19. Lithium silicate-diopside glass ceramic, which comprises 0.1 to 8.0 wt.-% $Al_2O_3$ and comprises lithium silicate as main crystal phase and diopside as further crystal phase.

20. Glass ceramic according to claim 19, which comprises 1.0 to 7.0 wt.-% $Al_2O_3$.

21. Glass ceramic according to claim 19, which comprises 2.0 to 5.0 wt.-% $Al_2O_3$.

22. Process for the preparation of dental restorations, wherein the glass ceramic according to claim 1 is given the shape of the desired dental restoration by pressing or machining.

23. Process according to claim 22, wherein the dental restoration is selected from bridge, inlay, onlay, veneer, abutment, partial crown, crown and shell.

* * * * *